United States Patent
Avalon et al.

(10) Patent No.: US 6,419,667 B1
(45) Date of Patent: Jul. 16, 2002

(54) STRETCHABLE MECHANICAL/ADHESIVE CLOSURE FOR A DISPOSABLE DIAPER

(75) Inventors: Gary A. Avalon, Painesville; William G. Hartman, North Royalton; Michael D. Hilston, Painesville; Karen L. Spilizewski, Euclid; David L. Savage, Painesville, all of OH (US)

(73) Assignee: Avery Dennison Corporation, Pasadena, CA (US)

( * ) Notice: Subject to any disclaimer, the term of this patent is extended or adjusted under 35 U.S.C. 154(b) by 0 days.

(21) Appl. No.: 09/101,564
(22) PCT Filed: Jan. 16, 1997
(86) PCT No.: PCT/US97/00720
§ 371 (c)(1),
(2), (4) Date: Oct. 9, 1998
(87) PCT Pub. No.: WO97/25892
PCT Pub. Date: Jul. 24, 1997

Related U.S. Application Data

(60) Provisional application No. 60/010,042, filed on Jan. 16, 1996.

(51) Int. Cl.$^7$ ............................ A61F 13/15; A44B 1/04; A44B 11/25; A44B 17/00
(52) U.S. Cl. .................. 604/391; 604/389; 604/386; 24/442
(58) Field of Search .................. 604/389, 391, 604/398, 386, 387; 24/442, 306, 444–448, 452, 550

(56) References Cited

U.S. PATENT DOCUMENTS 3,464,094 A  9/1969  Mates .................. 24/204

(List continued on next page.)

FOREIGN PATENT DOCUMENTS

EP  0 191 355  4/1989

*Primary Examiner*—John G. Weiss
*Assistant Examiner*—Michele Kidwell
(74) *Attorney, Agent, or Firm*—Pearne & Gordon LLP

(57) ABSTRACT

A fastening system for releasably securing a diaper provides both mechanical and adhesive or cohesive securement. Tab members comprise a facestock layer, a contact layer of adhesive or cohesive overlying at least a portion of the facestock layer, and mechanical fastening elements projecting from at least a portion of the contact layer. The facestock layer includes extensible and substantially nonextensible polymeric portions. A landing member includes complementary mechanical fastening elements and a contact surface or cohesive for engagement with the tab adhesive or cohesive. A method is also disclosed for making the fastening system.

15 Claims, 3 Drawing Sheets

U.S. PATENT DOCUMENTS

| | | | |
|---|---|---|---|
| 3,726,752 A | * 4/1973 | Provost | 161/67 |
| 3,800,796 A | 4/1974 | Jacob | 128/284 |
| 3,833,456 A | 9/1974 | Reed et al. | 161/167 |
| 3,932,328 A | 1/1976 | Korpman | 260/27 BB |
| 4,020,842 A | 5/1977 | Richman et al. | 128/287 |
| 4,051,853 A | 10/1977 | Egan, Jr. | 128/287 |
| 4,066,081 A | 1/1978 | Schaar | 128/287 |
| 4,239,829 A | 12/1980 | Cohen | 428/86 |
| 4,710,190 A | 12/1987 | Wood et al. | 604/389 |
| 4,787,897 A | * 11/1988 | Torimae et al. | 604/389 |
| 4,795,456 A | 1/1989 | Borgers et al. | 604/390 |
| 4,834,820 A | * 5/1989 | Kondo et al. | 156/73.3 |
| 4,869,724 A | 9/1989 | Scripps | 604/389 |
| 4,959,265 A | * 9/1990 | Wood et al. | 428/343 |
| 5,019,065 A | 5/1991 | Scripps | 604/385.1 |
| 5,053,028 A | 10/1991 | Zoia et al. | |
| 5,085,655 A | * 2/1992 | Mann et al. | 604/389 |
| 5,141,790 A | * 8/1992 | Calhoun et al. | 428/40 |
| 5,250,253 A | 10/1993 | Battrell | 264/557 |
| 5,279,604 A | 1/1994 | Robertson et al. | |
| 5,318,555 A | * 6/1994 | Siebers et al. | 604/390 |
| 5,549,591 A | 8/1996 | Landvogt | |
| 5,554,146 A | * 9/1996 | Niederhofer et al. | 604/391 |
| 5,554,239 A | * 9/1996 | Datta et al. | 156/66 |
| 5,605,735 A | * 2/1997 | Zehner et al. | 428/100 |
| 5,611,789 A | * 3/1997 | Seth | 604/391 |
| 5,636,414 A | * 6/1997 | Litchholt | 24/304 |
| 5,736,217 A | 4/1998 | Banfield et al. | 428/100 |
| 5,795,350 A | * 8/1998 | Schmitz | 604/391 |
| 5,916,207 A | * 6/1999 | Toyoda et al. | 604/391 |
| 6,007,527 A | * 12/1999 | Kawaguchi et al. | 604/386 |
| 6,030,373 A | * 2/2000 | VanGompel et al. | 604/386 |
| 6,063,466 A | * 5/2000 | Tuschy et al. | 428/40.1 |

\* cited by examiner

STRETCHABLE MECHANICAL/ADHESIVE CLOSURE FOR A DISPOSABLE DIAPER

This application claims the priority of U.S. Provisional Application No. 60/010,042, filed Jan. 16, 1996.

BACKGROUND OF THE INVENTION AND RELATED ART

The present invention relates to closures and methods of making closures for fastening adjacent portions or edges of materials or components together. The closures are useful as fastening system closures for disposable diapers.

Diapers of this general type are widely used. A typical diaper construction comprises an absorbent pad or batt or the like enclosed in an outer plastic shell or a non-woven backsheet that is non-woven fabric laminated with a water impermeable layer such as a polyethylene film. A water permeable inner shell or liner is also provided to promote separation of fluid from the user.

The fastener tape system generally includes adhesive tabs fastened to one end of the diaper assembly construction at each lateral side of the diaper in a permanent "factory joint" by the diaper manufacturer using adhesives or other techniques. The tabs have a face coated with pressure-sensitive adhesive. The tabs are releasably attachable to the other end of the diaper at each lateral side in a "user joint". The attachment is releasable both to allow permanent removal of the diaper and to allow unfastening to inspect the diaper followed by refastening if indicated.

The user joint may be formed by direct connection of the tab to the diaper outer surface whether the latter is formed of a plastic film or a non-woven backsheet. In the case of plastic film shells, it is typical to provide a "landing zone" formed of reinforcing tape or the like for receiving the end of the tab to form the user joint. The landing zone may provide a plastic surface or a non-woven surface and may comprise a knit type fabric landing pad.

The fastener tape system may rely solely upon pressure-sensitive adhesive in the formation of the user joint as shown in U.S. Pat. Nos. 4,795,456, 4,710,190, 4,020,842 and 3,833,456. The use of combined adhesive and mechanical fastener systems is shown in U.S. Pat. Nos. 5,019,065, 5,053,028 and 4,869,724. The teachings of all of these patents being incorporated herein by reference.

The use of extensible or stretchable tabs to promote user comfort through better fit and more secure mounting is also known in the art. The tabs operate as extensible diaper side waistbands. Examples of such diaper fastening systems are disclosed in U.S. Pat. Nos. 4,795,456, 4,066,081, 4,051,853 and 3,800,796.

Related art includes U.S. Pat. Nos. 3,464,094, 4,239,829, 5,250,253 and European Publication No. 0 191 355.

SUMMARY OF THE INVENTION

The present invention provides an extensible tab fastener system having a user joint that enables combined mechanical and adhesive attachment. The mechanical and adhesive attachments each contribute to the total integrity or strength of the diaper closure or user joint, and neither has to be fully effective to provide the required total closure strength. The tab fastener system may be produced by high speed manufacturing processes including coextrusion.

In the illustrated embodiments, the fastening system tab members comprise a facestock layer, a contact securement portion comprising a layer of adhesive or cohesive overlying at least a portion of the facestock layer, and mechanical fastening elements projecting from at least a portion of the contact layer. The tab contact securement portion extends over at least a portion of the extensible and substantially nonextensible polymeric portions of the facestock layer. A landing member includes complementary mechanical fastening elements and contact securement portion comprising a contact surface or cohesive for engagement with the tab adhesive or cohesive.

DETAILED DESCRIPTION OF THE INVENTION

Figure 2:
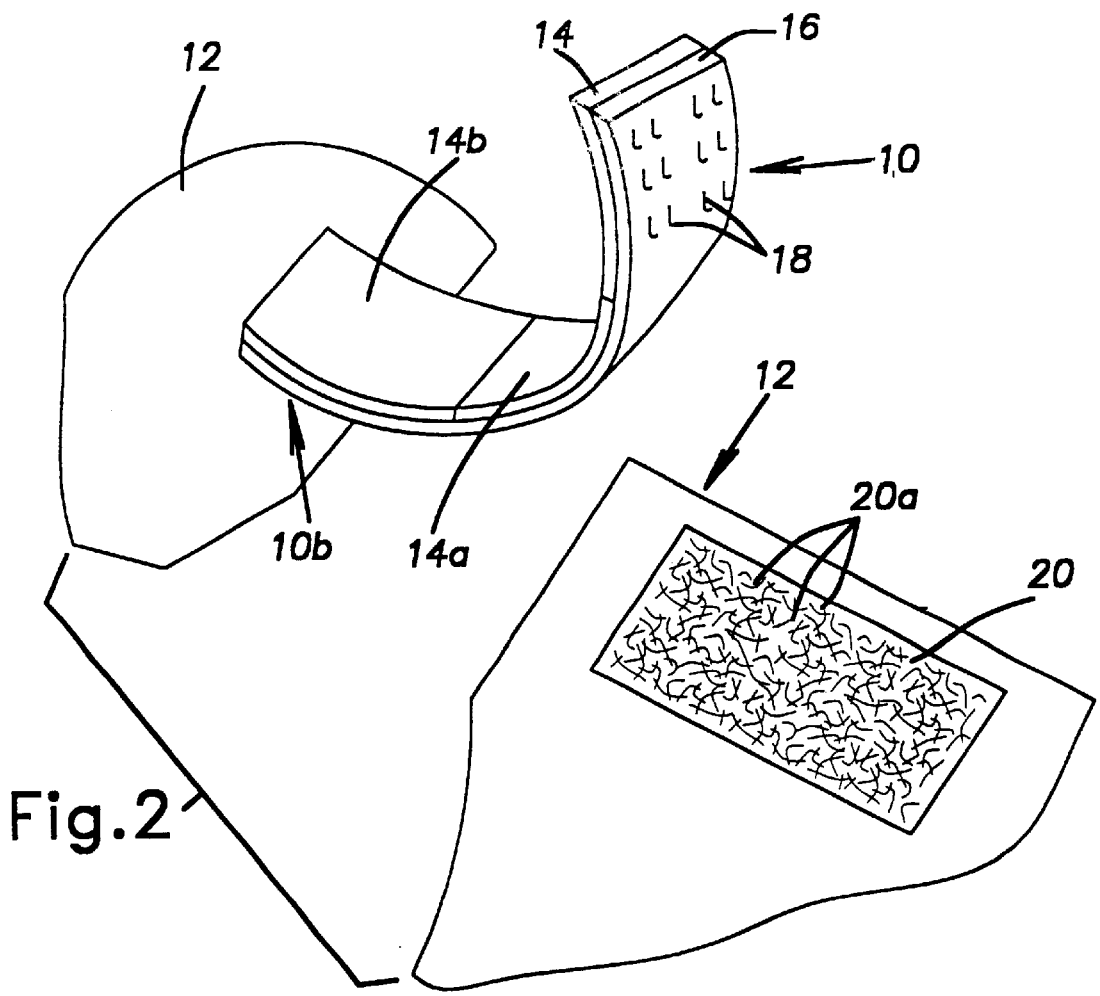
FIG. 2 is a fragmentary perspective view on a reduced scale showing the tab fastener system of FIG. 1 applied to a diaper with the tab in the deployed position ready for closure.
Figure 1:
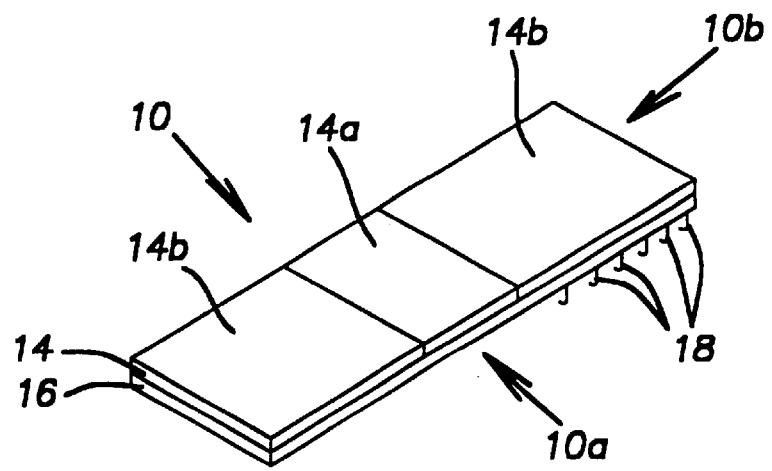
FIG. 1 is a perspective view of a tab fastener of a tab fastener system in accordance with the invention.

Referring to FIGS. 1 and 2, a diaper tab 10 for use in closure of a diaper 12 is shown. The diaper tab 10 includes a facestock film 14, an adhesive layer 16 and mechanical engagement or fastening elements 18.

The facestock film 14 includes an extensible central polymeric portion 14a and nonextensible terminal or polymeric portions 14b. The extensible portion 14a may be formed of elastomers such as the thermoplastic elastomers sold by the Shell Chemical Company under the designations Kraton. These elastomers may be SBS, SIS, SI, $S(IS)_x$ and SEBS block copolymers and mixtures thereof. The nonextensible portions 14b of the film 14 may be formed of polypropylene, polyethylene and combinations of such polymers having suitable film forming characteristics.

The adhesive layer 16 may be formed of known adhesive materials such as a pressure-sensitive adhesives including acrylic resin and natural or synthetic based rubber adhesives. Preferred adhesives include hot melt pressure-sensitive adhesives of the A-B-A block copolymer type comprising an elastomeric B-block derived from isoprene and thermoplastic A-blocks derived from styrene as disclosed in U.S. Pat. No. 3,932,328. Illustrative rubber based adhesives include styrene-isoprene-styrene and styrene-butadiene-styrene which may optionally contain diblock components such as styrene isoprene and styrene butadiene. The layer 16 may comprise a cohesive as taught in U.S. Pat. No. 5,085,655 to Mann, which patent is also owned by the assignee herein. The adhesives or cohesives may be applied using hot-melt, solvent or emulsion techniques. The adhesive or cohesive layer 16 may extend along a portion of or substantially all of the adjacent surface of the layer 14.

The elements 18 are integrally formed with the facestock film 14 in the illustrated embodiment. However, the elements 18 may be separately formed and attached to the surface of the facestock. The elements 18 extend generally perpendicular from the facestock film 14 and project through the adhesive layer 16. The protuberances provided by the projecting or exposed ends of the elements 18 should be of sufficient length to provide mechanical engagement with a locking or engaging array of elements, or with a fibrous material such as a non-woven landing tape or member 20 having fibers 20a as shown in FIG. 2 or a non-woven backsheet of a diaper. Further, the polymer forming the nonextensible portions 14b and the elements 18 should be of sufficient stiffness to provide the required shear strength engagement. It is preferred to dispose the elements 18 along only the nonextensible portions 14b since is believed to enhance the shear resistance by limiting tendency of the elements 18 to be laterally displaced.

The pressure-sensitive adhesive is relatively more extensible or stretchable than other adjacent layers, and the tab 10 has overall extensibility characteristics substantially corresponding with the facestock film 14. That is, the tab 10 includes a central elastic portion 10a corresponding with the location of the portion 14a and nonextensible terminal portions 10b corresponding with the locations of portions 14b. As shown, each of the portions 14a and 14b extend across the width of the tab 10 at spaced locations along the length of the tab extending between the end portions of the diaper to be joined.

Referring to FIG. 2, one of the terminal portions 10b of the tab 10 is secured to the diaper 12 at a factory joint at one of the lateral sides at one end of the diaper 12. The other terminal portion 10b is deployable to form a user joint with the landing tape 20 to close the diaper about a wearer such as an infant. It should be appreciated that the tab 10 may be provided with nonextensible facestock portions adjacent each end thereof to facilitate the provision of the factory joint with the diaper at one end and the manipulation of the tab to form the user joint at the other end.

The tab 10 and the landing member 20 provide a fastener system having both mechanical and adhesive engagement. During use, the elements 18 particularly provide shear strength and the pressure-sensitive adhesive layer particularly provides tack strength. This may be achieved with the adhesive bond between the pressure-sensitive adhesive layer 16 and the fibrous surface of the landing member 20. If the layer 16 is a cohesive, then the landing member 20 must also include the cohesive as a coating having the fibers 20a extending therethrough, discrete cohesive particles carried by the fibers 20a or as a separate cohesive area.

Figure 3:
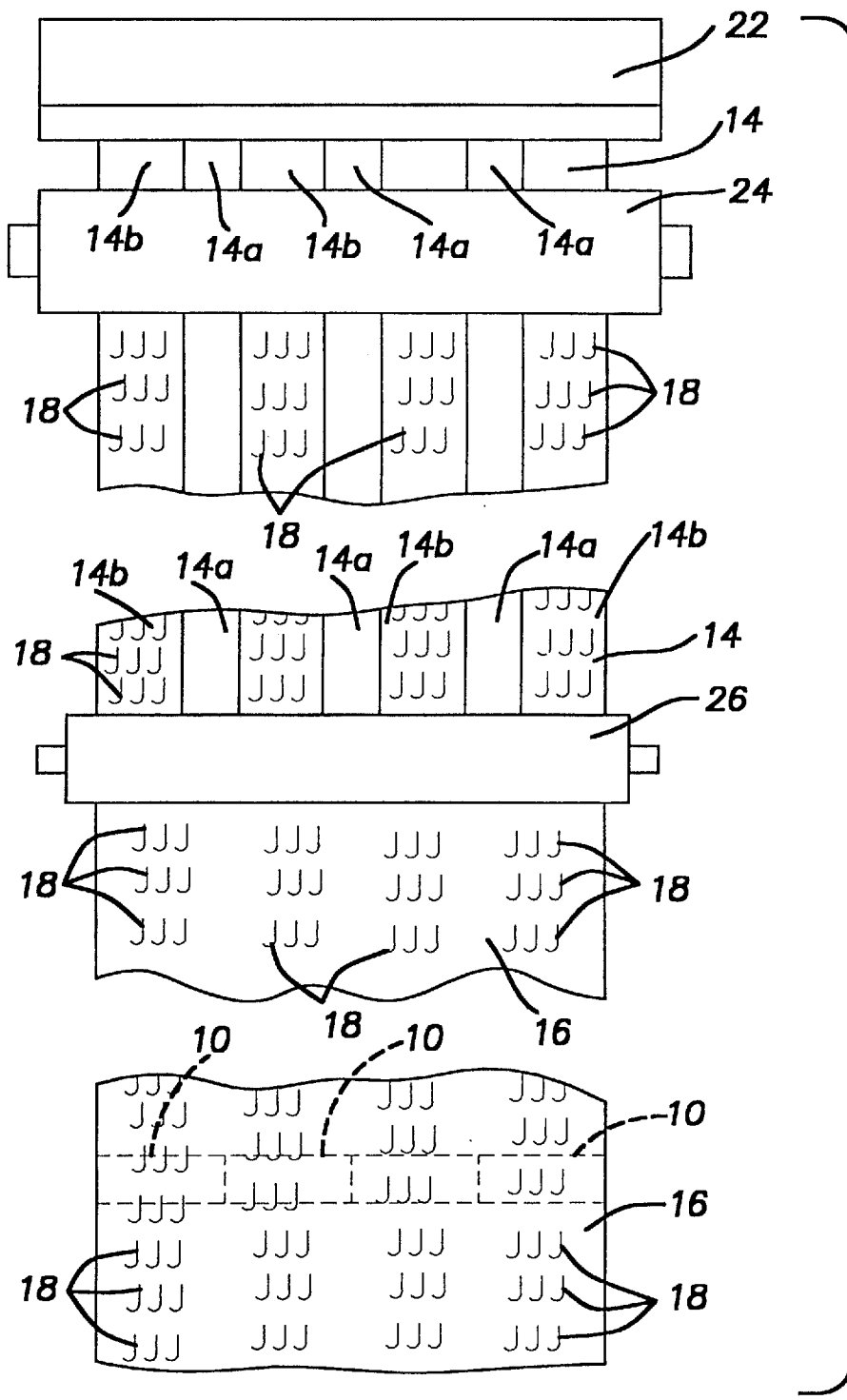
FIG. 3 is a fragmentary schematic plan view showing the process for making a tab fastener in accordance with the invention.

Referring to FIG. 3, a coextrusion die 22 extrudes the facestock film 14 as a side-by-side coextrusion including adjacent portions 14a and 14b. For convenience, the film 14 is shown to include a limited number of adjacent extensible and nonextensible portions, however, a much larger number of such portions may be provided along the width or cross direction of the film 14.

The film 14 upon exiting the die 22 engages a molding-casting roll 24 for purposes of further shaping the film. In this instance, the roll 24 cooperates with the die to form mechanical engagement elements 18 at least along the nonextensible portions 14b. The elements 18 may have a variety shapes such as hooks or mushrooms as are well known in the art. Fibrous hook and loop engagement elements are preferred.

The coextrusion processing requires a matching or near matching of the melt flow characteristics of the plastic materials forming the portions 14a and 14b. Such matching and processing techniques are known in the art and illustrated, for example, in U.S. Pat. No. 3,800,796.

The adhesive layer 16 is applied to the facestock film 14 along the surface having the elements 18 extending therefrom. As indicated above, the thickness of the adhesive layer 16 assures a sufficient projection of the elements 18 to effect mechanical engagement. The adhesive may be applied at the time of the manufacture of the film 14 or at a later time and, in either case, known techniques may be used with regulation of thickness to assure projection of elements 18. An adhesive coating roll 26 is shown in FIG. 3 applying the adhesive layer 16 to the film 14.

As shown by the dotted outline in FIG. 3, the film 14 having the adhesive layer 16 applied thereto is subsequently cut in the cross direction, as by a diaper manufacturer, to provide tabs 10. Each of tabs 10 has a central extensible portion 10a and nonextensible terminal portions 10b as described above. For convenience of illustration, the film 14 is shown to correspond in width with three tabs 10. In practice, the film 14 may have a width corresponding with a much larger number of tabs.

Figure 4:
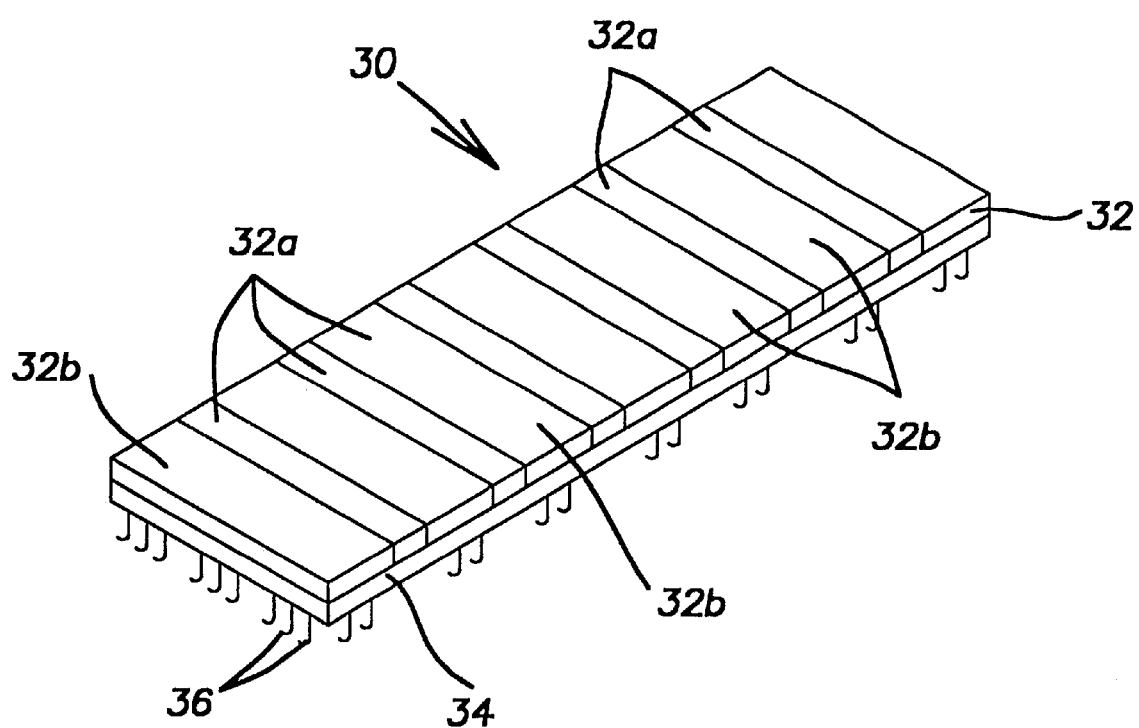
FIG. 4 is a perspective view similar to FIG. 1 showing a tab fastener in accordance with another embodiment of the invention.

Referring to FIG. 4, a tab 30 includes a facestock layer 32, an adhesive layer 34 and mechanical engagement elements 36. In the tab 30, a plurality of extensible portions 32a are provided along the length of the tab. As compared with the tab 10, the tab 30 is similarly extensible, but it does not have a single central extensible portion. Further, the elements 36 in the tab 30 are located along the entire surface of the adhesive layer 34. However, the elements 36 may be positioned along only the nonextensible portions 32b in a similar manner as in the above described embodiment.

While the invention has been shown and described with respect to particular embodiments thereof, this is for the purpose of illustration rather than limitation, and other variations and modifications of the specific embodiments herein shown and described will be apparent to those skilled in the art all within the intended spirit and scope of the invention. Accordingly, the patent is not to be limited in scope and effect to the specific embodiments herein shown and described nor in any other way that is inconsistent with the extent to which the progress in the art has been advanced by the invention.

What is claimed is:

1. A fastening system for releasably securing a diaper closed about a user includes tab and landing members respectively mounted to opposite ends of said diaper, each of said tab members including a facestock layer comprising a coextrusion of extensible and substantially nonextensible polymeric portions, first contact securement means comprising a first contact layer of pressure-sensitive adhesive or cohesive overlying said facestock layer, and first mechanical fastening elements comprising discrete members extending within and projecting from said first contact layer overlying said nonextensible portion of said facestock layer only, said landing member including second mechanical fastening elements for mechanical interengagement with said first mechanical fastening elements and second contact securement means comprising a second contact layer of pressure-sensitive adhesive or cohesive for adhesive or cohesive contact securement with said first contact layer, whereby said tab and landing member provide mechanical interengagement and simultaneous adhesive or cohesive securement when said fastening system secures said diaper about a user.

2. A fastening system as in claim 1, wherein said first and second mechanical fastening elements respectively comprise hooks and loops.

3. A fastening system as in claim 2, wherein said loops also provide said second contact securement means.

4. A fastening system as in claim 1, wherein said first contact layer is a layer of pressure-sensitive adhesive.

5. A fastening system as in claim 1, wherein said first contact layer is a layer of cohesive.

6. A fastening system as in claim 5, wherein said second contact layer is a layer of cohesive.

7. A fastening system as in claim 1, wherein said landing member comprises a fibrous fabric having fibers providing said second mechanical fastening elements.

8. A fastening system as in claim 7, wherein said fibers also provide said second contact securement means.

9. A fastening system as in claim 1, wherein said discrete members of said first mechanical fastening elements are formed separate of said first contact layer.

10. A fastening system as in claim 9, wherein said discrete members of said first mechanical fastening elements are partially embedded in said first contact layer.

11. A method of making a fastening system for releasably securing a diaper about a user, said fastening system including tab and landing members respectively mounted to opposite ends of said diaper, comprising:

providing a laminate for forming said tab member by coextruding a facestock layer including extensible and substantially nonextensible polymeric portions, applying a first contact layer of pressure-sensitive adhesive or cohesive over said facestock layer, and providing first mechanical fastening elements comprising discrete members extending within and projecting from said first contact layer overlying said nonextensible portion of said facestock layer only, cutting said laminate to form said tab member with a length and a width such that said polymeric portions extend substantially across the width of said tab member at spaced locations along the length thereof, providing said landing member including second mechanical fastening elements for mechanical interengagement with said first mechanical fastening elements and second contact securement means comprising a second contact layer of pressure-sensitive adhesive or cohesive for adhesive or cohesive contact securement with said first contact layer, and mounting said tab and landing members to said opposite ends of said diaper, whereby said tab and landing member provide mechanical interengagement and simultaneous adhesive or cohesive securement when said fastening system secures said diaper about a user.

12. A method as in claim 11, wherein said landing member comprises a fibrous fabric having fibers providing said second mechanical fastening elements.

13. A method as in claim 12, wherein said fibers also provide said second contact layer and said first contact layer is a layer of pressure-sensitive adhesive.

14. A method of as in claim 11, wherein said first contact layer has a thickness and an exposed surface remote of said facestock layer, and providing said first mechanical fastening elements includes providing said discrete members separate of said first mechanical fastening elements and attaching said discrete members to the facestock layer with said discrete members of said first fastening elements extending through said exposed surface of said first contact layer.

15. A method as in claim 11, wherein said first contact layer has a thickness and an exposed surface remote of said face stock layer, and providing said first mechanical fastening elements includes integrally providing said first mechanical fastening elements and said face stock layer with said discrete members of said first mechanical fastening elements extending through said exposed surface of said first contact layer.

* * * * *